(12) United States Patent
Colosimo et al.

(10) Patent No.: US 11,571,135 B1
(45) Date of Patent: Feb. 7, 2023

(54) SYSTEM AND METHOD FOR MULTIPLEXING AN OPTICAL SENSOR

(71) Applicant: Apple Inc., Cupertino, CA (US)

(72) Inventors: Joseph William Colosimo, Sunnyvale, CA (US); Tao Shui, Cupertino, CA (US); Brian R. Land, Woodside, CA (US)

(73) Assignee: Apple Inc., Cupertino, CA (US)

( * ) Notice: Subject to any disclaimer, the term of this patent is extended or adjusted under 35 U.S.C. 154(b) by 300 days.

(21) Appl. No.: 16/917,824

(22) Filed: Jun. 30, 2020

(51) Int. Cl.
| A61B 5/024 | (2006.01) |
| A61B 5/1455 | (2006.01) |
| A61B 5/00 | (2006.01) |
| G01V 8/20 | (2006.01) |

(52) U.S. Cl.
CPC ...... *A61B 5/02416* (2013.01); *A61B 5/14552* (2013.01); *A61B 5/681* (2013.01); *A61B 5/6886* (2013.01); *A61B 5/7203* (2013.01); *G01V 8/20* (2013.01)

(58) Field of Classification Search
CPC . A61B 5/02416; A61B 5/14552; A61B 5/681; A61B 5/6886; A61B 5/7203; G01V 8/20
See application file for complete search history.

(56) References Cited

U.S. PATENT DOCUMENTS

| 8,655,425 | B2 | 2/2014 | Kim et al. | |
| 9,184,863 | B2 | 11/2015 | Hosoda | |
| 10,602,937 | B2 | 3/2020 | Pekonen et al. | |
| 2004/0247223 | A1 | 12/2004 | Tietjen | |
| 2018/0344181 | A1* | 12/2018 | Schroeder | A61B 5/02438 |
| 2019/0317598 | A1 | 10/2019 | Aleem et al. | |

* cited by examiner

*Primary Examiner* — Unsu Jung
*Assistant Examiner* — Philip C Edwards
(74) *Attorney, Agent, or Firm* — Kubota & Basol LLP

(57) ABSTRACT

An optical sensor can be multiplexed for different clients/features including estimating information or characteristics of a user's physiological signals. Additionally, the clients/features can include estimating information or characteristics independent from a user's physiological signals. As the number of clients increase and/or as the requirements for the clients increase, flexibility can be provided to accommodate the various clients. Parallelization of the optical sensor can be used to improve performance as the number of clients increase. For example, the hardware and software architecture can assemble patterns of time slots that measure all desired light paths for the multiple clients and distribute the corresponding measurements to each client according to the client requests. In some examples, the scanning sequence can be represented by frames including slots associated with multiple clients to compress the representation for larger or more complex scan sequences.

33 Claims, 9 Drawing Sheets

SCAN SEQUENCE SETTINGS FIELDS

| FIELD NAME | DESCRIPTION |
|---|---|
| FINAL_SEGMENT | NUMBER OF SEGMENT PATTERNS MINUS 1 |
| SEG_0_FRAME | ID OF THE FRAME TO EXECUTE FOR SEGMENT 0 |
| SEG_0_REPS | NUMBER OF ADDITIONAL REPETITIONS OF THE SEGMENT |
| SEG_1_FRAME | ID OF THE FRAME TO EXECUTE FOR SEGMENT 1 |
| SEG_1_REPS | NUMBER OF ADDITIONAL REPETITIONS OF THE SEGMENT |
| ... | ... |
| SEG_N-1_FRAME | ID OF THE FRAME TO EXECUTE FOR SEGMENT N-1 |
| SEG_N-1_REPS | NUMBER OF ADDITIONAL REPETITIONS OF THE SEGMENT |

FRAME SETTINGS FIELDS

| FIELD NAME | DESCRIPTION |
|---|---|
| FINAL_SLOT | NUMBER OF SLOTS MINUS 1 IN THE FRAME |
| S0_PARAMSET | ID OF PARAMETER SET TO USE IN SLOT 0 |
| S1_PARAMSET | ID OF PARAMETER SET TO USE IN SLOT 1 |
| ... | ... |
| S_J-1_PARAMSET | ID OF PARAMETER SET TO USE IN SLOT J-1 |

PARAMETER SET FIELDS

| FIELD NAME | DESCRIPTION |
|---|---|
| LED_ID | ID OF LED |
| LED_CURRENT | LED CURRENT |
| ... | ... |

SEQUENCE SETTINGS

FRAME SETTINGS: F0, F1, ..., F_M-1

PARAMETER SETS: P0, P1, ..., P_K-1

*FIG. 5*

SYSTEM AND METHOD FOR MULTIPLEXING AN OPTICAL SENSOR

FIELD

This relates generally to systems and methods for multiplexing an optical sensor, and more particularly, to multiplexing an optical sensor for disparate usages including estimating information or characteristics of a user's physiological signals.

BACKGROUND

Optical sensors can be used to implement various features. The features can include estimating information or characteristics of a user's physiological signals. For example, the information or characteristics can include various measures of heart rate and/or arterial oxygen saturation, among other possibilities. Additionally, the features can include estimating information or characteristics independent from a user's physiological signals. For example, an optical sensor in a wearable device such as a watch can be used to detect contact with a user's wrist, termination of contact with the user's wrist, and/or contact with a non-wrist surface (e.g., a table, pocket, etc.)

SUMMARY

This relates to systems and methods for multiplexing an optical sensor, and more particularly, to multiplexing an optical sensor for disparate usages including estimating information or characteristics of a user's physiological signals. For example, one or more optical sensor may be used to implement several features (also referred to herein as "clients"). The features/clients can include estimating information or characteristics of a user's physiological signals. For example, the information or characteristics can include various measures of heart rate (e.g., motion-tolerant heart rate measurement, resting or static heart rate measurement, tachogram measuring user's heartbeat, etc.), arrhythmia detection, and/or arterial oxygen saturation, among other possibilities. Additionally, the features can include estimating information or characteristics independent from a user's physiological signals. For example, an optical sensor in a wearable device such as a watch can be used to detect contact with a user's wrist, termination of contact with the user's wrist, and/or contact with a non-wrist surface (e.g., a table, pocket, etc.). Parallelization of the optical sensor can be used to improve performance as the number of clients increase. The systems and method described herein relate to the architecture (e.g., hardware and underlying software infrastructure) to serve these clients. As the number of clients increase and/or as the requirements for the clients increase, flexibility can be provided to accommodate the various clients. In some examples, multiple clients can be served in parallel. The hardware and software architecture can assemble patterns of time slots that measure all desired light paths for the multiple clients and distribute the corresponding measurements to each client according to the client requests. In some examples, the scanning sequence can be represented by frames including slots associated with multiple clients to compress the representation for larger or more complex scan sequences.

BRIEF DESCRIPTION OF THE DRAWINGS

FIG. 5 illustrates a representation of the scan sequence using segments according to examples of the disclosure.

DETAILED DESCRIPTION

Figure 1A:
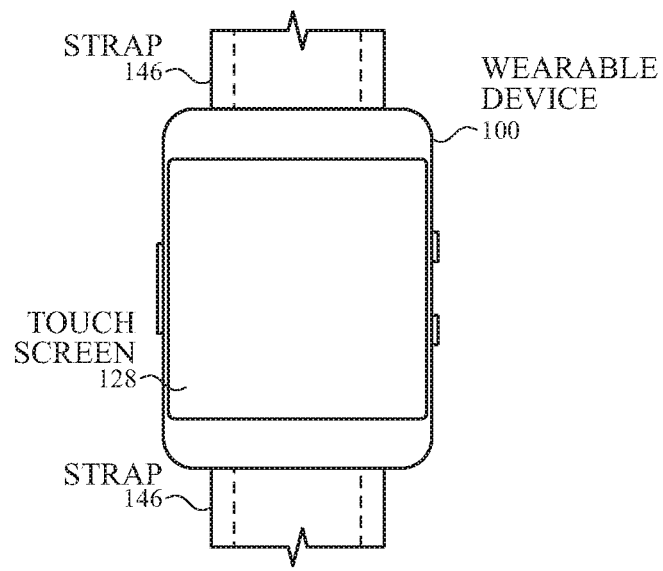
FIGS. 1A-1B illustrate views of an exemplary electronic device including one or more optical sensors according to examples of the disclosure.

In the following description of examples, reference is made to the accompanying drawings in which it is shown by way of illustration specific examples that can be practiced. It is to be understood that other examples can be used and structural changes can be made without departing from the scope of the various examples.

This relates to systems and methods for multiplexing an optical sensor, and more particularly, to multiplexing an optical sensor for disparate usages including estimating information or characteristics of a user's physiological signals. The optical sensor may operate in one or more measurement modes for one or more features (also referred to herein as "clients"), each measurement mode designed to obtain measurements of one or more light paths under a particular set of circumstances (e.g., feature-specific scanning rate, light paths, parameter sets, etc.) that reflect the requirements of the feature. The features/clients can include estimating information or characteristics of a user's physiological signals. For example, the information or characteristics can include various measures of heart rate (e.g., motion-tolerant heart rate measurement, resting or static heart rate measurement, tachogram measuring user's heartbeat, etc.), arrhythmia detection, and/or arterial oxygen saturation, among other possibilities. Additionally, the features can include estimating information or characteristics independent from a user's physiological signals. For example, an optical sensor in a wearable device such as a watch can be used to detect contact with a user's wrist, termination of contact with the user's wrist, and/or contact with a non-wrist surface (e.g., a table, pocket, etc.).

In some examples, the optical sensor may be used to implement several features. In some such examples, the optical sensor may operate in a first measurement mode for a first feature, in a second mode for a second feature, and so on. In some examples, parallelization of the optical sensor can be used to improve performance as the number of clients increase. The systems and methods described herein relate to the architecture (e.g., hardware and underlying software infrastructure) to serve these clients. As the number of clients increase and/or as the requirements for the clients increase, flexibility can be provided to accommodate the various clients. In some examples, multiple clients can be served in parallel. The hardware and software architecture can assemble patterns of time slots that measure all desired light paths for the multiple clients (and under the particular sets of circumstances required under the various measurement modes) and distribute the corresponding measurements to each client according to the client requests. In some examples, the scanning sequence can be represented by frames including slots associated with multiple clients to compress the representation for larger or more complex scan sequences.

As described herein, a scan sequence can include a number of "beats," and each beat in the scan sequence can be initiated with a regular cadence (e.g., 64 Hz, 128 Hz, 256 Hz, 512 Hz, etc.) The "beat cadence" can describe the fundamental fastest measurement cadence for the scan sequence. Each beat of the scan sequence can include one or more "time slots" (also referred to herein as "slots"), optionally followed by an idle period. Each of the time slots can define a portion of the beat during which the optical sensor can drive one or more LEDs and sense one or more photodetectors (selected and configured according to "parameter sets"). In some examples, a "frame" can define a pattern of time slots to be performed during beat configured according to the frame. In some examples, "segments" can define an order of frames and a number of repetition of the frames in a scan sequence. In other words, a segment describes the configuration of one or more consecutive beats in a scan sequence such that all beats within that segment have an identical configuration according to a frame.

Figure 1C:
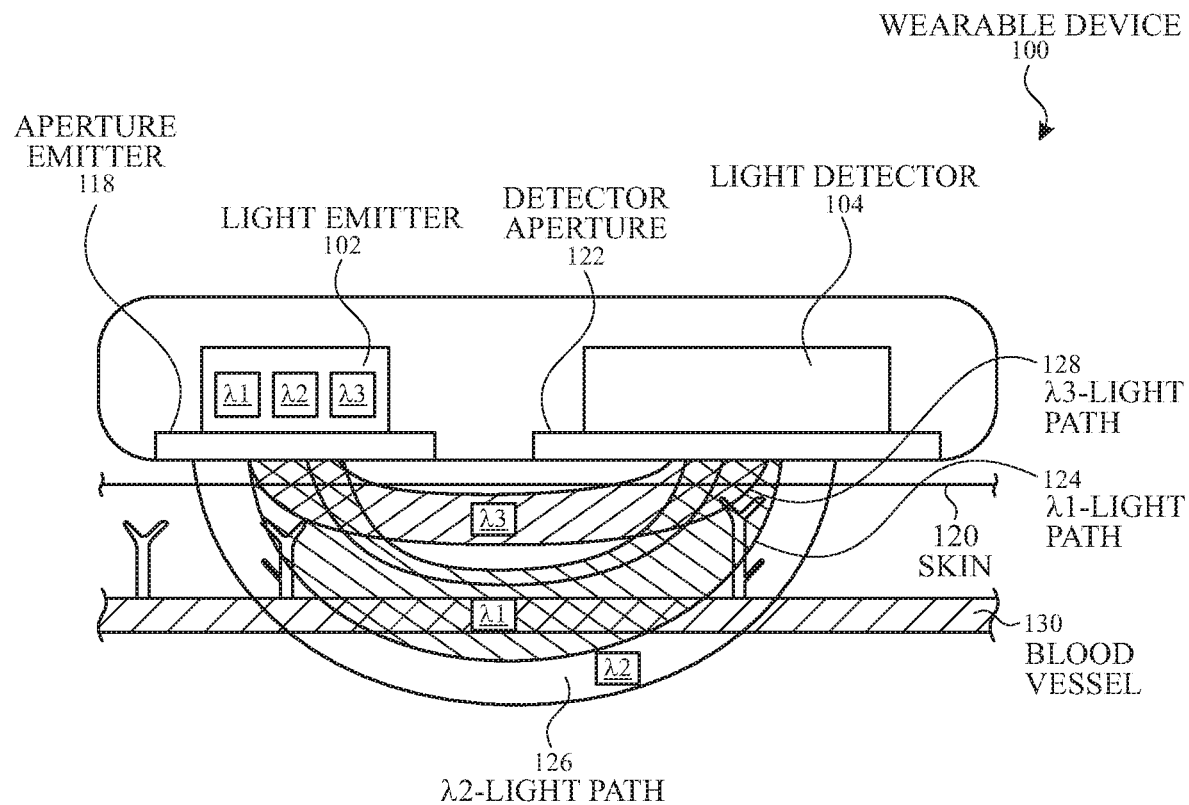
FIG. 1C illustrates a cross-sectional view of exemplary wearable device including one or more light emitters and one or more light detectors according to examples of the disclosure.
Figure 1B:
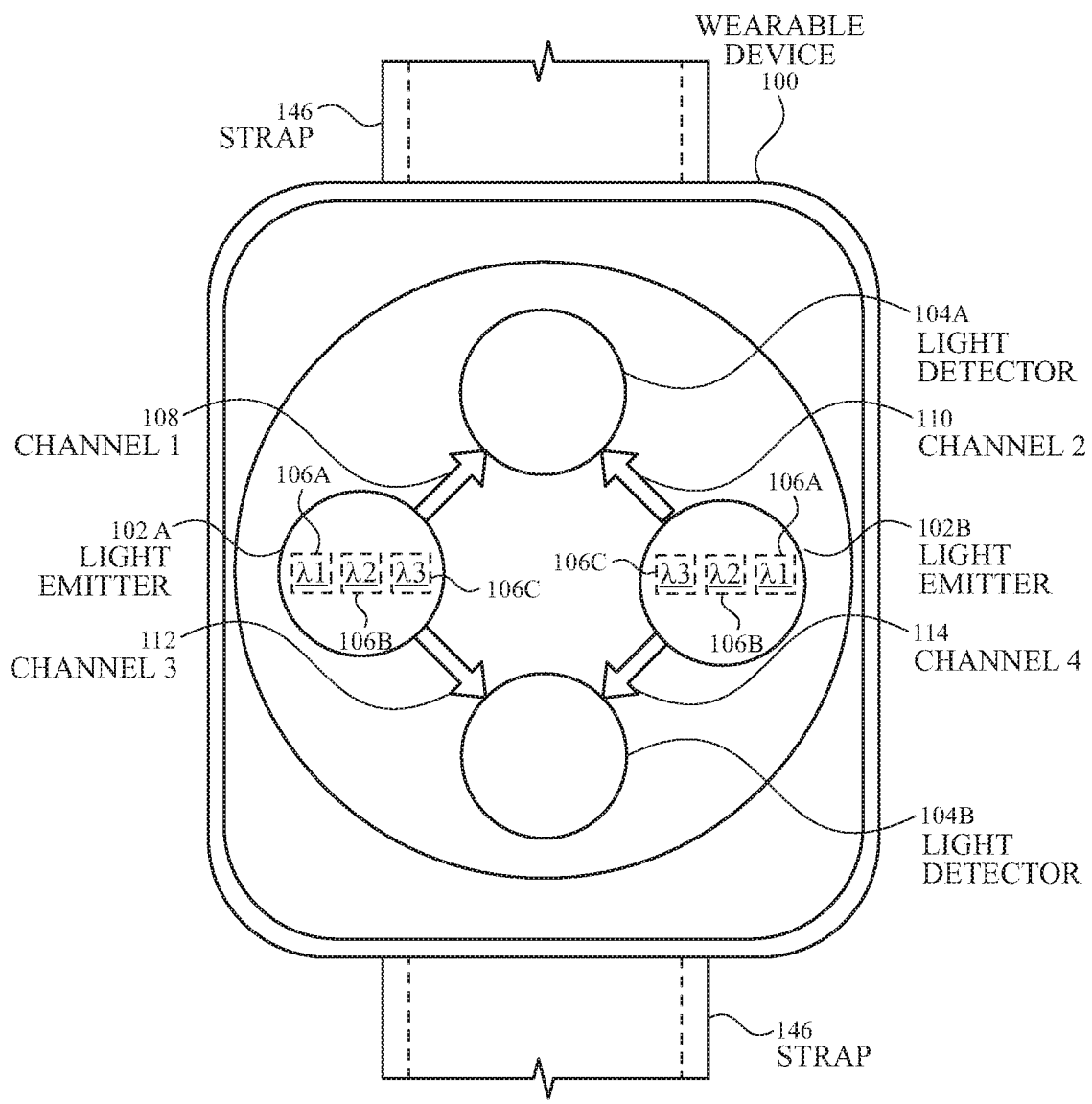

FIGS. 1A-1B illustrate views of an exemplary electronic device including one or more optical sensors according to examples of the disclosure. FIG. 1A illustrates a top view of an exemplary wearable device 100 that can include a touch screen 128 and can be attached to a user using a strap 146 or other fastener. FIG. 1B illustrates a bottom view (underside) of exemplary wearable device 100 including one or more optical sensors comprising one or more light emitters and one or more light detectors according to examples of the disclosure. For example, FIG. 1B illustrates device 100 that can include light emitters 102A-B and light detectors 104A-B. Device 100 can be positioned such that light emitters 102A-B and light detectors 104A-B are proximate to a user's skin or any other tissue site. For example, device 100 can be held in the user's hand or strapped to the user's wrist, among other possibilities. In some examples, light emitters 102A-B and light detectors 104A-B can be in close proximity (e.g., within a threshold distance, such as 5 mm, for example) to the surface of user's skin or can be physically contacting a surface of user's skin, which can reduce the amount of detected light that has not traveled through tissue.

In some examples, light emitters 102A-B can include one or more light sources to generate light at different wavelengths. For example, FIG. 1B illustrates each light emitter 102A-B including three light sources 106A-C (e.g., light emitting diodes (LEDs) or organic light emitting diodes (OLEDs)) configured to generate light at at least wavelengths $\lambda 1$, $\lambda 2$, and $\lambda 3$, respectively. Although three wavelengths are shown, in some examples, device 100 may include light sources at fewer or more wavelengths. Additionally, in some examples, each light emitter can include one light source with a tunable wavelength (e.g., voltage or current controlled) or with different filters, rather than using a different light source for each wavelength. In some examples, each light emitter 102A-B can be optically coupled to each light detector 104 for each wavelength. For example, light emitter 102A can be optically coupled to both light detectors 104A-B and light emitter 102B can be optically coupled to both light detectors 104A-B. Light emitter 102A can be configured to emit light (at one or more wavelengths) and generate one or more light paths detected by light detector 104A and one or more light paths detected by light detector 104B. Light emitter 102B can also be configured to emit light (at one or more wavelengths) and generate one or more light paths detected by light detector 104A and one or more light paths detected by light detector 104B. As illustrated in FIG. 1B, a first channel 108 can be used to measure signal at light detector 104A from light emitter 102A (at each respective wavelength), a second channel 110 can be used to measure signal at light detector 104A from light emitter 102B (at each respective wavelength), a third channel 112 can be used to measure signal at light detector 104B from light emitter 102A (at each respective wavelength), and a fourth channel 114 can be used to measure signal at light detector 104B from light emitter 102B (at each respective wavelength). The measured signal at each detector can include light measured from various light paths (e.g., through the skin and/or air) between the respective emitter and detector of the channel.

Device 100 can also include processing circuitry to process light detected from light detectors 104A-B. In some examples, the processing circuitry can be used to determine the user's physiological signals and extract information (e.g., one or more characteristics) from the physiological signals. In some examples, a physiological characteristic can be one or more measures of heart rate or a hemoglobin oxygen saturation level (e.g., an arterial oxygen saturation ($SpO_2$)). In some examples, the processing circuitry can remove or reduce motion artifacts from the physiological signals to account for non-cardiac-induced pulsatile blood volume changes. In some examples, the processing circuitry can process light detected from light detectors 104A-B for functions independent from determining the user's physiological signals.

FIG. 1C illustrates a cross-sectional view of exemplary wearable device 100 including one or more light emitters and one or more light detectors according to examples of the disclosure. As illustrated in FIG. 1C, light emitter 102 can generate light at one or more wavelengths that can exit aperture 118 (e.g., a window). The light can be directed towards, and incident upon, the user's skin 120 and some of the light can be returned back toward device 100 (e.g., reflected and/or scattered from interacting with the skin). The light can reenter device through aperture 122 (e.g., a window) and be detected by light detector 104. In some examples, apertures 118 and 122 (and thereby light emitter 102 and light detector 104) can be in close proximity (e.g., within a threshold distance, such as 5 mm, 1 mm, 0.1 mm, etc.) to the surface of user's skin or can be physically contacting a surface of user's skin, which can reduce the amount of detected light that has not traveled through tissue. A portion of light can be absorbed by molecules in skin 120, vasculature, and/or blood. Pulsatile blood flow in the user can lead to changes in the arterial vessel diameters, tissue hemoglobin concentration or volume, red blood cell orientation, velocity, or other physical states during a pressure change (e.g., diastole to systole), which can be included in light (e.g., via a scattering or absorption contrast mechanism) within the field of view of light detector 104. In some examples, heart rate can be estimated based on the changes in the detected light at one or more wavelengths due to pulsatile blood flow. In some examples, oxygen saturation in the blood can be estimated based on a ratio between physiological signal measurements (e.g., light intensity signals at light detectors) at two (or more) wavelengths. For example, oxygen saturation can be estimated based on a relative modulation ratio at two or more wavelengths. In some examples, the modulation ratio can be a perfusion index (PI) ratio based on physiological signal measurements at two or more wavelengths. Although the intensity of the physiological signal (or more generally the magnitude of each independent wavelength measurement) may change due to variations in the pulsations of blood, movement and the heterogeneity of tissue, the relative modulation ratio (e.g., between red light and infrared light) can be relatively stable indicator of oxygen saturation (e.g., via an empirical mapping between the relative modulation ratio and oxygen saturation).

In some examples, the signals from the one or more light emitters and one or more light detectors can be utilized to perform other functions aside from measuring the user's physiological signals and extracting information/characteristics from the physiological signals. For example, one or more light emitters and one or more light detectors can be configured for monitoring whether or not the device remains in contact with a user's skin (e.g., on-wrist and/or off-wrist detection) and/or whether the device is in contact with a non-skin surface such as a table.

FIG. 1C illustrates exemplary optical paths for three different wavelengths $\lambda 1$, $\lambda 2$ and $\lambda 3$. Optical path 124 can correspond to wavelength $\lambda 1$ (e.g., in the wavelength range of 620 nm-750 nm) and optical path 126 can correspond to wavelength $\lambda 2$ (e.g., in the wavelength range of 750 nm-1400 nm). In some examples, wavelength $\lambda 1$ can be in the range of visible light (e.g., 400 nm-700 nm) and wavelength $\lambda 2$ can be in the range of near-infrared (NIR) light (e.g., 700-1100 nm), which can be strongly absorbed by blood and other molecules in the user's tissue and blood. In some examples, wavelength $\lambda 1$ can be red light and wavelength $\lambda 2$ can be IR light. Optical path 128 can correspond to wavelength $\lambda 3$ (e.g., in the wavelength range of 495 nm-570 nm). In some examples, $\lambda 3$ can be in a lower wavelength range of visible light (e.g., 400 nm-495 nm), such as blue light, or near ultraviolet light (e.g., 300 nm-400 nm), or other portions of the visible light, NIR, short-wave IR spectra. It should be understood that these wavelength ranges are for exemplary purposes and different wavelength ranges are possible for $\lambda 1$, $\lambda 2$, and $\lambda 3$ (or any additional wavelengths). As shown in FIG. 1C, in some examples, different wavelengths can penetrate different depths within skin 120. For example, optical paths 124 and 126 corresponding to wavelengths $\lambda 1$ and $\lambda 2$ can penetrate more deeply within the skin 120 and underlying tissue, whereas optical path 128 corresponding to wavelength $\lambda 3$ can penetrate less deeply within skin 120 and the underlying tissue. Additionally, although the optical paths may penetrate different depths, it is understood that light at some wavelengths can penetrate a variety of depths including shallower and deeper within the tissue.

Skin 120 and underlying tissue can include the blood vessels (arterial and venous) such as blood vessel 130. Light emitter 102 and light sensor 104 can be located and wavelengths can be selected such that optical paths 124 and 126 corresponding to wavelengths $\lambda 1$ and $\lambda 2$ can be sensitive to arterial blood volume changes to enable an estimation of the characteristic of a user's physiological signals.

Figure 1D:
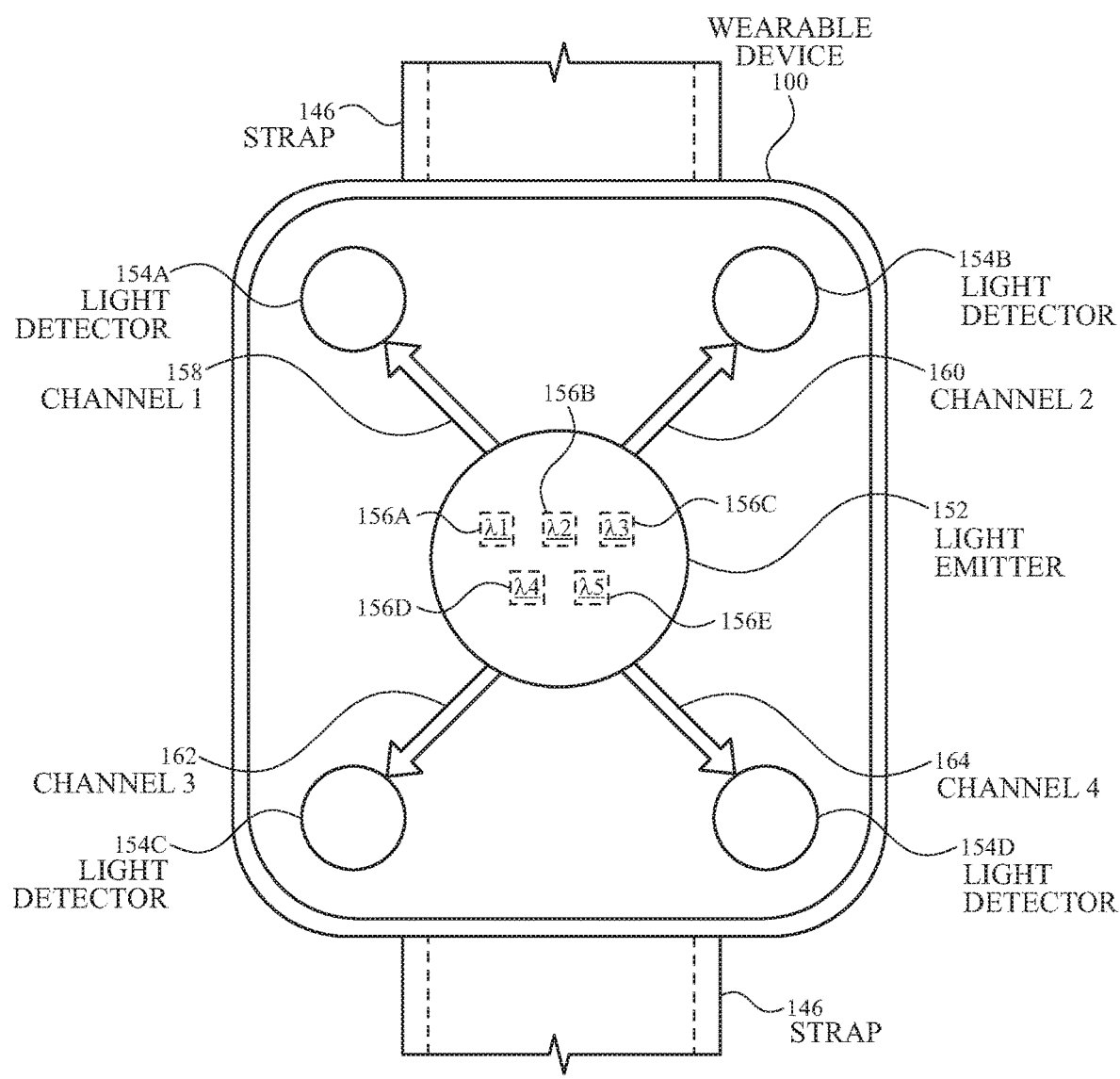
FIG. 1D illustrates an alternative arrangement of light emitters and light detectors on the underside of an exemplary electronic device according to examples of the disclosure.

FIG. 1D illustrates an alternative arrangement of light emitters and light detectors on the underside of an exemplary electronic device according to examples of the disclosure. FIG. 1D illustrates device 100 that can include light emitter 152 in a center of the device and light detectors 154A-D. Light emitter 152 can include one or more light sources to generate light at different wavelengths. For example, FIG. 1D illustrates light emitter 152 including five light sources 156A-E (e.g., an LED or OLED) configured to generate light at wavelengths $\lambda 1$, $\lambda 2$, $\lambda 3$, $\lambda 4$ and $\lambda 5$, respectively. Although five wavelengths are shown, in some examples, device 100 may include light sources at fewer or more wavelengths (or one tunable/filterable light source) or may include different types of light sources (e.g., laser diodes). Light emitter 152 can be optically coupled to one or more (or each of) light detectors 154A-D for one or more (or each of the) wavelengths. In some examples, light emitter 152 can be configured to emit light (at one or more wavelengths) and generate one or more light paths detected by light detector 154A, one or more light paths detected by light detector 154B, one or more light paths detected by light detector 154C and one or more light paths detected by light detector 154D. As illustrated in FIG. 1D, a first channel 158 can be used to measure signal at light detector 154A from light emitter 152 (e.g., at each respective wavelength), a second channel 160 can be used to measure signal at light detector 154A from light emitter 152 (at each respective wavelength), a third channel 162 can be used to measure signal at light detector 104C from light emitter 152 (at each respective wavelength), and a fourth channel 164 can be used to measure signal at light detector 154D from light emitter 152 (at each respective wavelength). The measured signal at each detector (at each respective wavelength) can include light that has traversed various light paths (e.g., through the skin and/or air) between the respective emitter and detector of the channel.

Although FIGS. 1B and 1D illustrate four channels (each operable for emitting/detecting light at multiple wavelengths), in some examples, fewer or additional channels may be implemented. For example, a single channel including one light emitter and one light detector can be used. In some examples, additional light emitters and/or light detectors may be used to form additional channels. For example, adding one or more additional light detectors to the configurations in FIG. 1B or 1D can increase the number of channels.

Figure 2A:
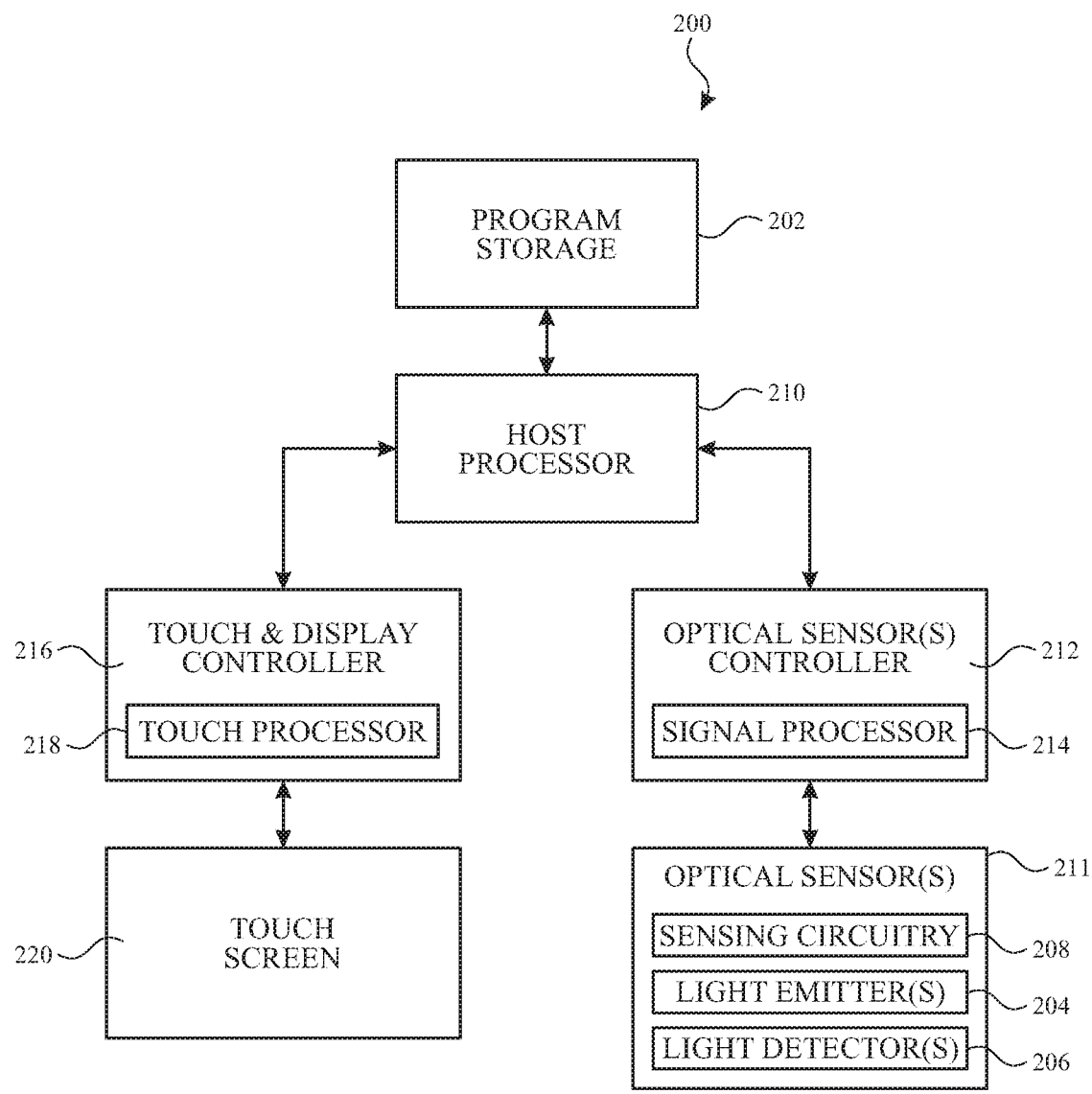
FIG. 2A illustrates an exemplary block diagram of a computing system including an optical sensor according to examples of the disclosure.

FIG. 2A illustrates an exemplary block diagram of a computing system including an optical sensor according to examples of the disclosure. Although primarily described herein as a wearable device, the computing system may alternatively be implemented partially or fully in a non-wearable device. For example, the sensors and/or processing described herein can be implemented partially or fully in a mobile telephone, media player, tablet computer, personal computer, server, etc. In some examples, the light emitters and light detectors can be implemented in a wearable device (e.g., a wristwatch) and the processing of the data can be performed in a non-wearable device (e.g., a mobile phone). Processing and/or storage of the physiological signals in a separate device can enable the device including the physiological sensors (e.g., a wristwatch) to be space and power efficient (which can be important features for portable/wearable devices).

Computing system 200 can correspond to device 100 illustrated in FIGS. 1A-1D (or may be implemented in other wearable or non-wearable electronic devices). Computing system 200 can include a processor 210 (or more than one processor) configured to execute instructions and to carry out operations associated with computing system 200. For example, using instructions retrieved from program storage 202, processor 210 can control the reception and manipulation of input and output data between components of computing system 200. Processor 210 can be a single-chip processor (e.g., an application specific integrated circuit) or can be implemented with multiple components/circuits.

In some examples, processor 210 together with an operating system can operate to execute computer code, and produce and/or use data. The computer code and data can reside within a program storage 202 that can be operatively coupled to processor 210. Program storage 202 can generally provide a place to hold data that is being used by computing system 200. Program storage block 202 can be any non-transitory computer-readable storage medium, and can store, for example, history and/or pattern data relating to PPG signals and relative modulation ratio (e.g., perfusion index ratio) values measured by a configuration of light emitter(s) 204 and light detector(s) 206 (e.g., as illustrated in FIG. 1B or 1D). By way of example, program storage 202 can include Read-Only Memory (ROM), Random-Access Memory (RAM), hard disk drive and/or the like. The computer code and data could also reside on a removable storage medium and loaded or installed onto computing system 200 when needed. Removable storage mediums include, for example, CD-ROM, DVD-ROM, Universal Serial Bus (USB), Secure Digital (SD), Compact Flash (CF), Memory Stick, Multi-Media Card (MMC) and/or a network component.

Computing system 200 can also include one or more input/output (I/O) controllers that can be operatively coupled to processor 210. I/O controllers can be configured to control interactions with one or more I/O devices (e.g., touch sensor panels, display screens, touch screens, physical buttons, dials, slider switches, joysticks, or keyboards). I/O controllers can operate by exchanging data between processor 210 and the I/O devices that desire to communicate with processor 210. The I/O devices and I/O controller can communicate through a data link. The data link can be a unidirectional or bidirectional link. In some cases, I/O devices can be connected to I/O controllers through wireless connections. A data link can, for example, correspond any wired or wireless connection including, but not limited to, PS/2, Universal Serial Bus (USB), Firewire, Thunderbolt, Wireless Direct, IR, RF, Wi-Fi, Bluetooth or the like.

For example, computing system 200 can include an optical sensor controller 212 operatively coupled to processor 210 and to one or more optical sensors 211. The optical sensor(s) can include light emitter(s) 204, light detector(s) 206 and corresponding sensing circuitry 208 (e.g., analog circuitry to drive emitters and measure signals at the detector, provide processing (e.g., amplification, filtering), and convert analog signals to digital signals). As described herein, light emitters 204 and light detectors 206 can be configured to generate and emit light into a user's skin and detect returning light (e.g., reflected and/or scattered) to measure a physiological signal (e.g., a PPG signal). The absorption and/or return of light at different wavelengths can also be used to determine a characteristic of the user (e.g., oxygen saturation, heart rate) and/or about the contact condition between the light emitters 204/light detectors 206 and the user's skin. Measured raw data from the light emitters 204, light detectors 206 and sensing circuitry 208 can be transferred to processor 210, and processor 210 can perform the signal processing described herein to estimate a characteristic (e.g., oxygen saturation, heart rate, etc.) of the user from the physiological signals. Processor 210 and/or optical sensor controller 212 can operate light emitters 204, light detectors 206 and/or sensing circuitry 208 to measure data from the optical sensor. In some examples, optical sensor controller 212 can include timing generation for light emitters 204, light detectors 206 and/or sensing circuitry 208 to sample, filter and/or convert (from analog to digital) signals measured from light at different wavelengths. Optical sensor controller 212 can process the data in signal processor 214 and report outputs (e.g., PPG signal, relative modulation ratio, perfusion index, heart rate, on-wrist/off-wrist state, etc.) to the processor 210. Signal processor 214 can be a digital signal processing circuit such as a digital signal processor (DSP). The analog data measured by the optical sensor(s) 211 can be converted into digital data by an analog to digital converter (ADC), and the digital data from the physiological signals can be stored for processing in a buffer (e.g., a FIFO) or other volatile or non-volatile memory (not shown) in optical sensor controller 212. In some examples, some light emitters and/or light detectors can be activated, while other light emitters and/or light detectors can be deactivated to conserve power, for example, or for time-multiplexing. In some examples, processor 210 and/or optical sensor controller 212 can store the raw data and/or processed information in memory (e.g., ROM or RAM) for historical tracking or for future diagnostic purposes. Additional detail regarding optical sensors and processing optical signals is described below.

Computing system 200 can also include, in some examples, a touch and display controller 216 operatively coupled to processor 210 and to touch screen 220. Touch screen 220 can be configured to display visual output in a graphical user interface (GUI), for example. The visual output can include text, graphics, video, and any combination thereof. In some examples, the visual output can include a text or graphical representation of the physiological signal (e.g., a PPG waveform) or a characteristic of the physiological signal (e.g., oxygen saturation, heart rate, etc.) Touch screen can be any type of display including a liquid crystal display (LCD), a light emitting polymer display (LPD), an electroluminescent display (ELD), a field emission display (FED), a light emitting diode (LED) display, an organic light emitting diode (OLED) display, or the like. Processor 210 can send raw display data to touch and display controller 216, and touch and display controller 216 can send signals to touch screen 220. Data can include voltage levels for a plurality of display pixels in touch screen 220 to project an image. In some examples, processor 210 can be configured to process the raw data and send the signals to touch screen 220 directly. Touch and display controller 216 can also detect and track touches or near touches (and any movement or release of the touch) on touch screen 220. For example, touch processor 218 can process data representative of touch or near touches on touch screen 220 (e.g., location and magnitude) and identify touch or proximity gestures (e.g., tap, double tap, swipe, pinch, reverse-pinch, etc.). Processor 210 can convert the detected touch input/gestures into interaction with graphical objects, such as one or more user-interface objects, displayed on touch screen 220 or perform other functions (e.g., to initiate a wake of the device or power on one or more components).

In some examples, touch and display controller 216 can be configured to send raw touch data to processor 210, and processor 210 can process the raw touch data. In some examples, touch and display controller 216 can be process raw touch data itself (e.g., in touch processor 218). The processed touch data (touch input) can be transferred from touch processor 218 to processor 210 to perform the function corresponding to the touch input. In some examples, a separate touch sensor panel and display screen can be used, rather than a touch screen, with corresponding touch controller and display controller.

In some examples, the touch sensing of touch screen 220 can be provided by capacitive touch sensing circuitry (e.g., based on mutual capacitance and/or self-capacitance). For example, touch screen 220 can include touch electrodes arranged as a matrix of small, individual plates of conductive material or as drive lines and sense lines, or in another pattern. The electrodes can be formed from a transparent conductive medium such as ITO or ATO, although other partially or fully transparent and non-transparent materials (e.g., copper) can also be used. In some examples, the electrodes can be formed from other materials including conductive polymers, metal mesh, graphene, nanowires (e.g., silver nanowires) or nanotubes (e.g., carbon nanotubes). The electrodes can be configurable for mutual capacitance or self-capacitance sensing or a combination of mutual and self-capacitance sensing. For example, in one mode of operation, electrodes can be configured to sense mutual capacitance between electrodes; in a different mode of operation, electrodes can be configured to sense self-capacitance of electrodes. During self-capacitance operation, a touch electrode can be stimulated with an AC waveform, and the self-capacitance to ground of the touch electrode can be measured. As an object approaches the touch electrode, the self-capacitance to ground of the touch electrode can change (e.g., increase). This change in the self-capacitance of the touch electrode can be detected and measured by the touch sensing system to determine the positions of one or more objects when they touch, or come in proximity to without touching, the touch screen. During mutual capacitance operation, a first touch electrode can be stimulated with an AC waveform, and the mutual capacitance between the first touch electrode and a second touch electrode can be measured. As an object approaches the overlapping or adjacent region of the first and second touch electrodes, the mutual capacitance therebetween can change (e.g., decrease). This change in the mutual capacitance can be detected and measured by the touch sensing system to determine the positions of one or more objects when they touch, or come in proximity to without touching, the touch screen. In some examples, some of the electrodes can be configured to sense mutual capacitance therebetween and some of the electrodes can be configured to sense self-capacitance thereof.

Note that one or more of the functions described herein, including measuring and processing physiological signals according to examples of the disclosure, can be performed by firmware stored in memory (or in program storage 202) and executed by physiological sensor controller 212, touch and display controller 216 or processor 210. The firmware can also be stored and/or transported within any non-transitory computer-readable storage medium for use by or in connection with an instruction execution system, apparatus, or device, such as a computer-based system, processor-containing system, or other system that can fetch the instructions from the instruction execution system, apparatus, or device and execute the instructions. In the context of this document, a "non-transitory computer-readable storage medium" can be any medium (excluding signals) that can contain or store the program for use by or in connection with the instruction execution system, apparatus, or device. The computer-readable storage medium can include, but is not limited to, an electronic, magnetic, optical, electromagnetic, infrared, or semiconductor system, apparatus or device, a portable computer diskette (magnetic), a random access memory (RAM) (magnetic), a read-only memory (ROM) (magnetic), an erasable programmable read-only memory (EPROM) (magnetic), a portable optical disc such a CD, CD-R, CD-RW, DVD, DVD-R, or DVD-RW, or flash memory such as compact flash cards, secured digital cards, USB memory devices, memory sticks, and the like.

The firmware can also be propagated within any transport medium for use by or in connection with an instruction execution system, apparatus, or device, such as a computer-based system, processor-containing system, or other system that can fetch the instructions from the instruction execution system, apparatus, or device and execute the instructions. In the context of this document, a "transport medium" can be any medium that can communicate, propagate or transport the program for use by or in connection with the instruction execution system, apparatus, or device. The transport medium can include, but is not limited to, an electronic, magnetic, optical, electromagnetic or infrared wired or wireless propagation medium.

Referring back to FIG. 1B, light emitters 102A-B can generate light and light detectors 104A-B can measure light at multiple wavelengths $\lambda 1, \lambda 2, \lambda 3$. In some examples, three light sources 106A-C can be co-located (within a threshold distance of one another, e.g., less than 5 mm) in each of light emitters 102A-B. In some examples, each of the light sources can be driven in a time-multiplexed manner. For example, during a measurement period of duration T (from time $t_0$ to $t_6$), a first light source 106A of light emitter 102A can be driven at wavelength $\lambda 1$ and light can be detected at light detectors 104A-B (from $t_0$ to $t_1$), a second light source 106B of light emitter 102A can be driven at wavelength $\lambda 2$ and light can be detected at light detectors 104A-B (from $t_1$ to $t_2$), a third light source 106C of light emitter 102A can be driven at wavelength $\lambda 3$ and light can be detected at light detectors 104A-B (from $t_2$ to $t_3$), a fourth light source 106A of light emitter 102B can be driven at wavelength $\lambda 1$ and light can be detected at light detectors 104A-B (from $t_3$ to $t_4$), a fifth light source 106B of light emitter 102B can be driven at wavelength $\lambda 2$ and light can be detected at light detectors 104A-B (from $t_4$ to $t_5$), and a sixth light source 106C of light emitter 102B can be driven at wavelength $\lambda 3$ and light can be detected at light detectors 104A-B (from $t_5$ to $t_6$). Ideally, the measurement period can be less than a threshold duration. Reducing the duration of measurement period can allow for the measurements at different wavelengths to be as co-located in time as possible. In some examples, the duration of the measurement period can be less than 100 ms. The above measurements can result in a sample for each channel (e.g., four channels of FIG. 1B) at each wavelength (e.g., $\lambda 1, \lambda 2, \lambda 3$) for the measurement period. As described in more detail herein, other scan sequences can be used to operate the optical sensor to perform one or more functions at one or more sampling rates.

Figure 2B:
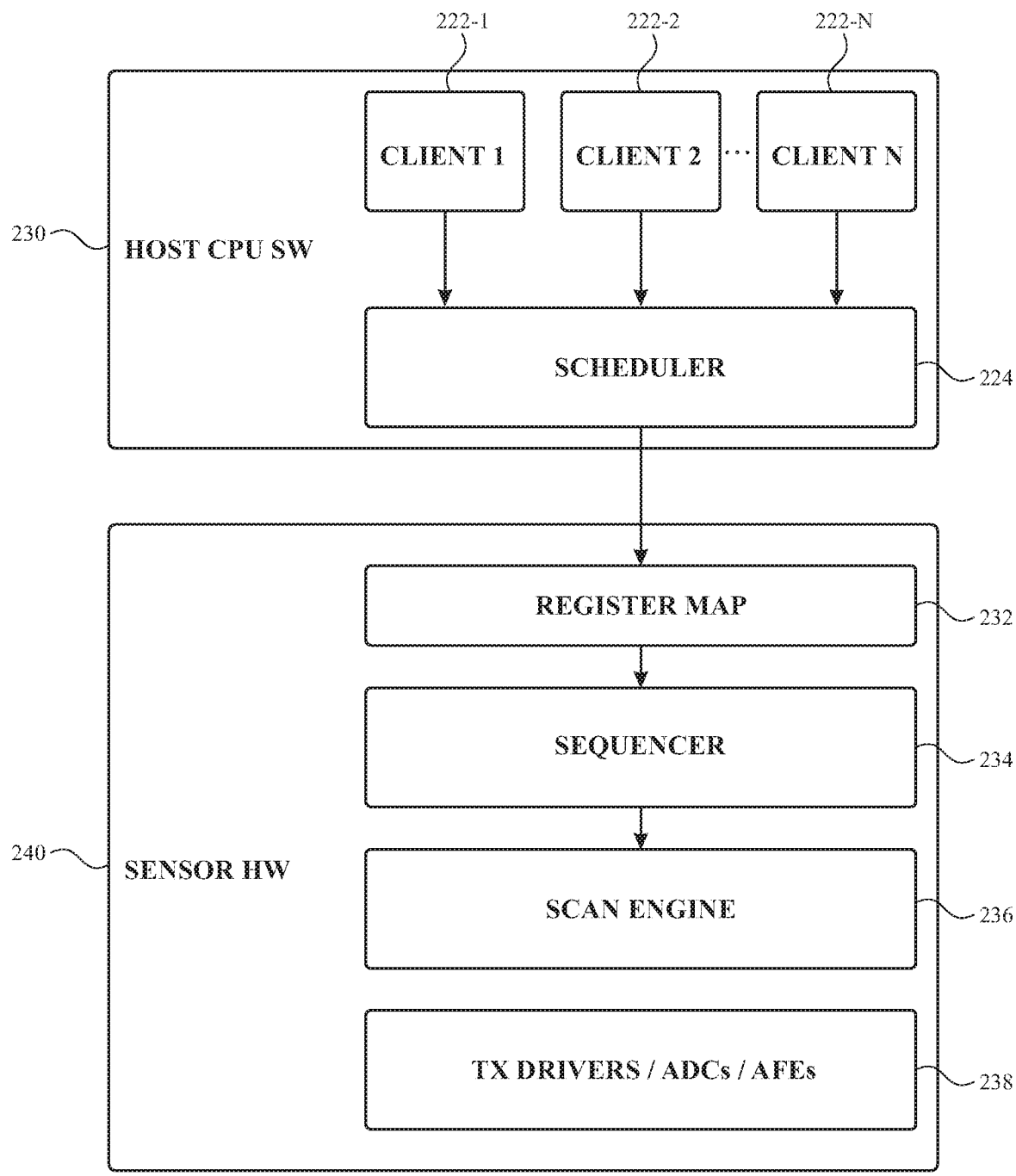
FIG. 2B illustrates an exemplary architecture of some components of a computing system according to examples of the disclosure.

FIG. 2B illustrates an exemplary architecture of some components of computing system 200 according to examples of the disclosure. FIG. 2B illustrates a software module 230 implemented by a processor (e.g., corresponding to processor 210 and/or processor 214) and hardware circuitry 240 (e.g., corresponding to optical sensor controller 212 and/or sensing circuitry 208). For example, software module 230 includes a representation of software entities including multiple clients 221_1, 222_2, 222_N and scheduler 224. Each of the multiple clients corresponds to a measurement mode using one or more light paths of an optical sensor (e.g., corresponding to optical sensor 211) under specified circumstances for the client. For example, each of the clients can request one or more light path measurements (each light path specifying an emitter and detector) with different scanning rate requirements. In some examples, clients that request a large number of light paths with relatively low scanning rate can coexist with clients that request a small number of light paths with relatively high scanning rate. The client request can be made with the scheduler 224 via an application programming interface (API). Scheduler 224 can use the clients' requirements (e.g. measurement modes) to produce a scan sequence that can be sent to hardware circuitry 240 (e.g., by writing registers in a register map 232) via a communication bus (e.g., inter-integrated circuit (I2C) bus, serial peripheral interface (SPI) bus, or other wired or wireless communication channel). The communication bus can also be used to transfer data from the light path measurements back to the clients (in a raw or processed format). Scheduler 224 can determine the number of beats required for the scan sequence and the slots required for each beat in the scan sequence. Scheduler 224 can assemble the parameter sets (e.g., identifying light path and drive/sense parameters) for each slot, and assemble for each beat a frame according to the required slot. In some examples, scheduler 224 can assemble the scan sequence according to the frame required for each beat (e.g., each beat can be configured according to an identified frame). In some examples, scheduler 224 can assemble the scan sequence according to segments defining an order of frames and one or more additional repetitions of the frames (e.g., beats 1-4 of the scan sequence can be performed according to a first segment defining a first frame and three additional repetitions, beat 5 can be performed according to a second segment defining a second frame and no additional repetitions, beats 6-8 can be performed according to a third segment defining the first frame and two additional repetitions, and beats 9 and 10 can be performed according to a fourth segment defining a third frame with one additional repetition). Whether to define the scan sequence using frames or segments defining patterns of frames can be a trade-off between memory and design-complexity, among other considerations. Scheduler 224 can produce the scan sequence using an algorithm in some examples. In some examples, scheduler 224 can produce the scan sequence using a lookup table of known client interactions. The scan sequence can include an assignment of frames for the beats (and/or a pattern of scan segments defining frames and a number of repetition of the frames) and/or the configurations for the time slots of the frames. The details of the scan sequence are described further below. In some examples, some of the clients can request one or more light path measurements common to (e.g., shared by) multiple clients. Scheduler 224 can identify the common light path measurement(s) to avoid duplication of the common light path measurement, and the common measurement results can be shared with the multiple clients (e.g., via scan engine 236).

Hardware circuitry 240 can include register map 232, sequencer 234, scan engine 236 and driving/sensing circuitry 238 (e.g., corresponding to sensing circuitry 308). The driving/sensing circuitry 238 can include drivers (Tx drivers) to drive the emitters (e.g., corresponding to light emitters 204), analog front-end (AFE) circuitry to measure detectors (e.g., corresponding to light detector(s) 206) and ADCs to convert the analog signals from the AFEs to digital signals. The register map 232 can store the scan sequence in a plurality of registers (e.g., logic circuits, such as D flip-flops, etc.). Sequencer 234 (e.g., implemented in hardware logic circuitry) can be configured to maintain knowledge of the current beat of the scan sequence, and can be configured to extract the set of parameters from register map 232 that may be required for each slot of the current beat in the scan sequence, and to provide the set of parameters to scan engine 236 (e.g., implemented in hardware logic circuitry). Scan engine 236 can receive the set of parameter for each slot in the beat and can execute the light path measurement (or multiple light path measurements) for each slot of the beat. For example, the set of parameters can include parameters for the driving/sensing circuitry. At the beginning of a sampling period, the optical sensor can apply power to the optical sensor to drive (e.g., illuminated the selected LED with a selected modulation pattern) and sense (e.g., measuring one or more photodiodes in parallel) the optical sensor for each time slot (according to the configuration for the optical sensor dictated by the parameter set for the respective slot). Once the measurements are performed for the time slots, the optical sensor can be powered down (e.g., during an idle period) until the next sampling period. Scan engine 236 can also provide results from all the light path measurements for the beat (e.g., at the conclusion of the beat).

FIGS. 3A-3D illustrate example timing representations of scan sequences according to examples of the disclosure. Exemplary timing representations 300, 310, 320 and 330 represent scan sequences with each row representing a beat and each rectangle representing a time slot (or slot). A light path measured in each slot can be represented by the selected LED, where "L0" represents an LED with identifier "0," "L1" represents an LED with identifier "1," and so on. It is understood that although the example timing representations of FIGS. 3A-3D show one selected LED for each slot, in some examples, multiple LEDs and/or multiple light paths may be measured during a slot. Additionally, the shading associated with the slots can indicate the client associated with the slot. Although not shown in FIGS. 3A-3D, the slots in each beat can be followed by idle periods (e.g., such that each row and subsequent idle period can represent the same period of time in the scan sequence, thereby achieving the uniform beat cadence).

Figure 3A:
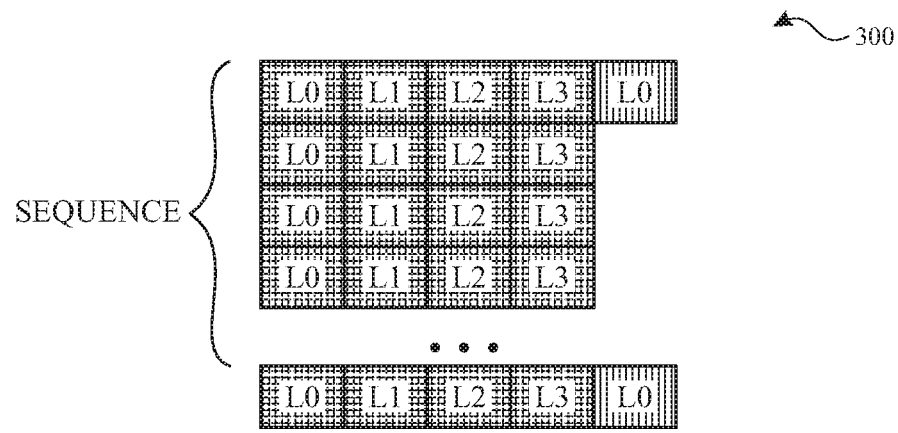
FIGS. 3A-3D illustrate example timing representations of scan sequences according to examples of the disclosure.

FIG. 3A illustrates an example timing representation 300 of a scan sequence according to examples of the disclosure. Timing representation 300 can correspond to two clients operating at two different scanning rates. A first client can correspond to a physiological signal client operating for each beat, and can involve measuring light paths corresponding to L0-L3 during four slots. The first client may be a single physiological signal client selected from a number of available physiological signal clients (e.g., motion-tolerant heart rate monitoring, static heart rate monitoring, tachogram measuring timing of user's heartbeat, arterial oxygen saturation, etc.) A second client can correspond to a wrist-detection client, and can involve measuring L0 during a fifth slot. The measurement of L0 for the second client may involve different parameters than for the measurement of L0 for the first client (e.g., different wavelength, different drive current, different AFE settings such as receiver gain, etc.). The first client can operate at a first scanning rate (e.g., at the beat cadence) and the second client can operate at a second scanning rate different from the first scanning rate. Specifically, the second scanning rate be achieved by measuring the light path corresponding to L0 in the fifth slot every N beats, such that the second scanning rate can be equal to the first scanning rate (the beat cadence) divided by N (where N can be an integer). For example, measuring L0 for the second client (e.g., in the fifth slot) every fourth beat results in a second scanning rate that is a quarter of the first scanning rate (the beat cadence). Likewise, measuring L0 for the second client every eighth beat results in a second scanning rate that is an eighth of the first scanning rate (the beat cadence).

Figure 3B:
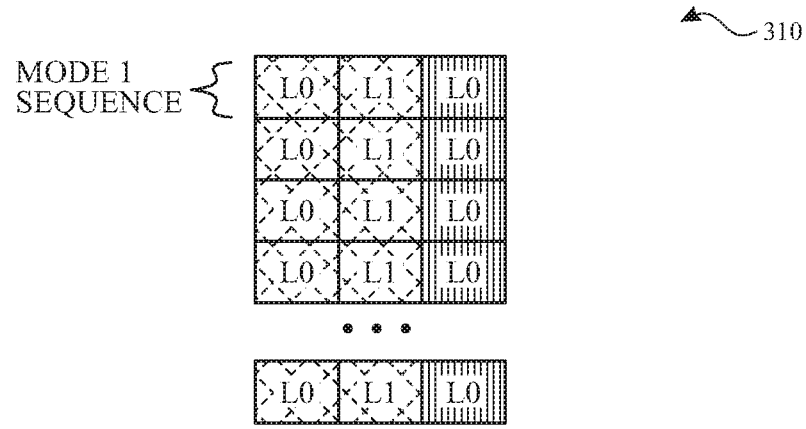
Figure 3C:
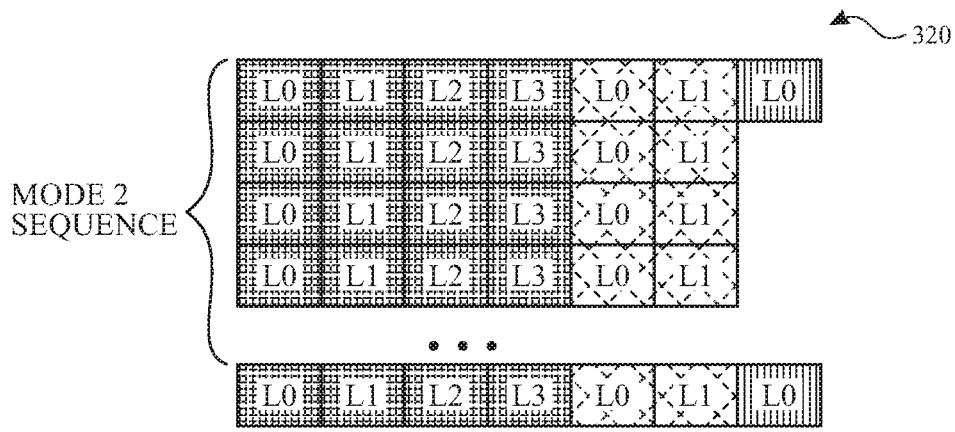

As described above, the scan sequence described with respect to FIG. 3A enables one physiological signal client to be operated during a beat. In some examples, a system can operate in multiple modes to enable one or more physiological signal clients to be operated during a beat. FIGS. 3B and 3C illustrate example timing representation 310 corresponding to a first scan sequence in a first mode of operation and example timing representation 320 corresponding to a second scan sequence in a second mode of operation according to examples of the disclosure. The first mode of operation can correspond to operation of two clients with a common scanning rate. For example, a first client (e.g., a physiological signal client) can involve measuring L0 and L1 during two slots and a second client (e.g., a wrist detection mode) can involve measuring L0 during a third slot. The measurements for the first client and the second client can be performed during each beat in the first mode of operation, such that the first scanning rate and the second scanning rate can be the same scanning rate.

The second mode of operation can correspond to operation of three clients with two different scanning rates. A first client (e.g., a first physiological signal client) can involve measuring L0-L4 during four slots, and a second client (e.g., a second physiological signal client) can involve measuring L0 and L1 during two slots (e.g., slots five and six). The measurement of L0 and L1 for the second client may involve the same or different parameters than for the measurement of L0 and L1 for the first client (e.g., different wavelength, different drive current, different AFE settings such as receiver gain, etc.). The measurements for the first and second clients can be performed during each beat in the second mode of operation, such that the first scanning rate corresponding to the first client and the second scanning rate corresponding to the second client can be the same scanning rate (e.g., the beat cadence). A third client (e.g., corresponding to a wrist-detection client) can involve measuring L0 during a slot (e.g., the seventh slot). The measurement of L0 for the third client may involve the same or different parameters than for the measurement of L0 for the first or second clients (e.g., different wavelength, different drive current, different AFE settings such as receiver gain, etc.). The third client can operate at a third scanning rate different from the first and second scanning rates. Specifically, in a similar manner as described with respect to FIG. 3A, the measurements for the third client can be repeated every N beats such that the third scanning rate can be equal to 1/N times the first or second scanning rate.

Figure 3D:
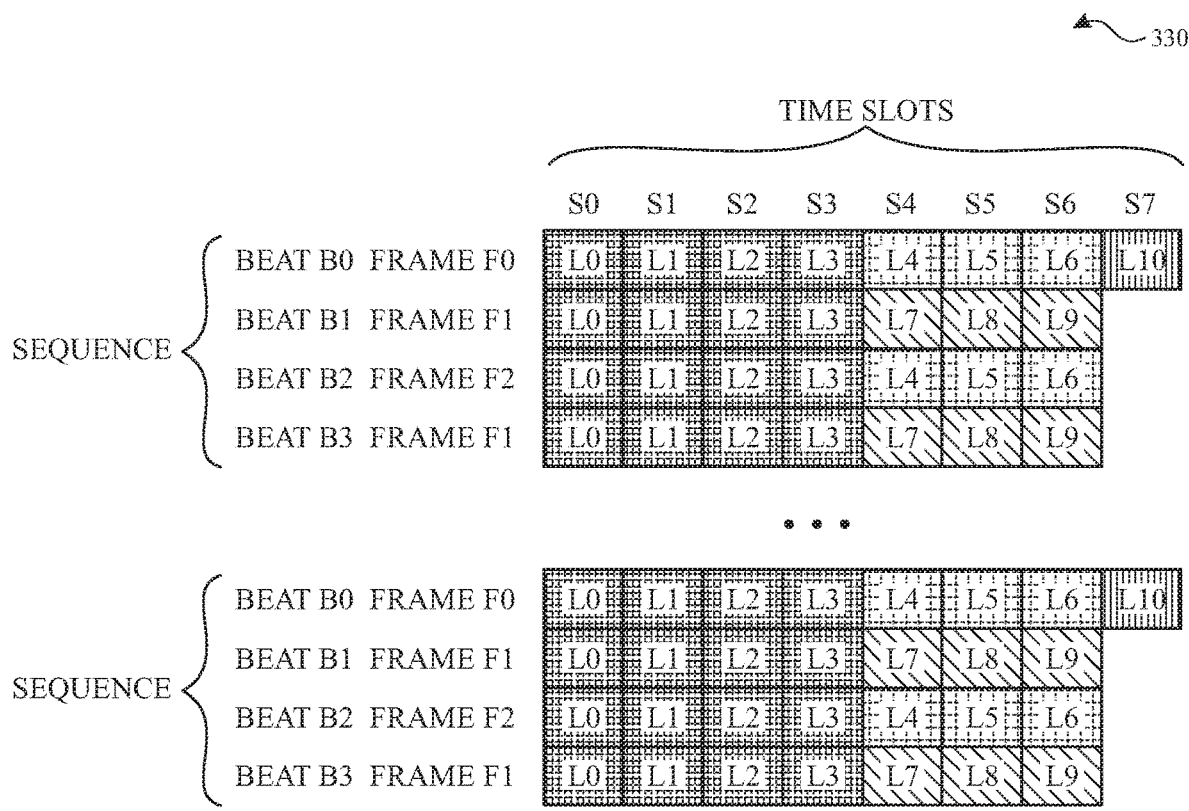

In some examples, the system can use scan sequences to enable multiple clients including physiological signal clients with different scanning rates. FIG. 3D illustrates an example timing representation 330 corresponding to a scan sequence including multiple physiological signal clients with different scanning rates according to examples of the disclosure. FIG. 3D can correspond to operation of three clients with three different scanning rates. A first client (e.g., a first physiological signal client) can involve measuring L0-L4 and can have a first scanning rate (e.g., the beat cadence). A second client (e.g., a second physiological signal client) can involve measuring L4-L9 and can have a second scanning rate (different from the first scanning rate). A third client (e.g., a wrist-detection client) can involve measuring L10 and can have a third scanning rate (different than the first and the second scanning rate). In the example illustrated in FIG. 3D, the second sampling rate can be half of the first scanning rate, and the third scanning rate can be a quarter of the first scanning rate (because it repeats once every four beats). A scanning sequence can be constructed (e.g., by scheduler 224) to achieve these scanning rates desired by the various clients. In particular, measurements for the first client with the highest scanning rate can be performed during each beat (e.g., at the beat cadence), measuring L0-L4 in four slots.

Measurements for the second client, with the next highest scanning rate (half the first scanning rate, in this example), can be performed across two beats. For example, L4-L6 can be measured for the second client in three slots (e.g., slots five to seven) during alternating beats (e.g., beats B0 and B2), and L7-L9 can be measured for the second client in three slots (e.g., slots five to seven) during alternating beats (e.g., beats B1 and B3). Measurements for the third client can be performed every fourth beat in the eight slot.

Although FIG. 3D divides the measurements for the second client between two beats, the second scanning rate can be alternatively achieved by measuring L4-L9 in every other beat. For example, the second scanning rate can be achieved by measuring L4-L9 in six slots in the first beat and in the third beat (corresponding to beats B1 and B3), and measuring L10 for the third client in an eleventh slot (rather than an eight slot) every four beats. However, such an arrangement may extend the length of the beat compared with the arrangement of the sequence illustrated in FIG. 3D, which may limit the frequency of the first scanning rate (e.g., the beat cadence). In some examples, the scheduler can use an algorithm to determine the sequence for multiple client requests executed by the software subsystem. In some examples, the scheduler algorithm can optimize the schedule for certain parameters. For example, the scheduler can optimize for reducing the maximum size of the beats and thereby increasing the beat cadence (to enable higher frequency scanning rates). In some examples, the scheduler can optimize for reducing the number of unique segment patterns. For example, the scan sequence in FIG. 3D includes three different patterns for the beats, referred to herein as frames, with one frame repeating for two separate beats. Frame F0, includes slots for L0-L6 and L10, frame F1 includes slots for L0-L3 and L7-L9, and frame F2 includes slots for L0-L6. Frame F1 may be repeated in the sequence for the second beat and the fourth beat (e.g., beats B1 and B3), as shown in FIG. 3D.

Figure 4:
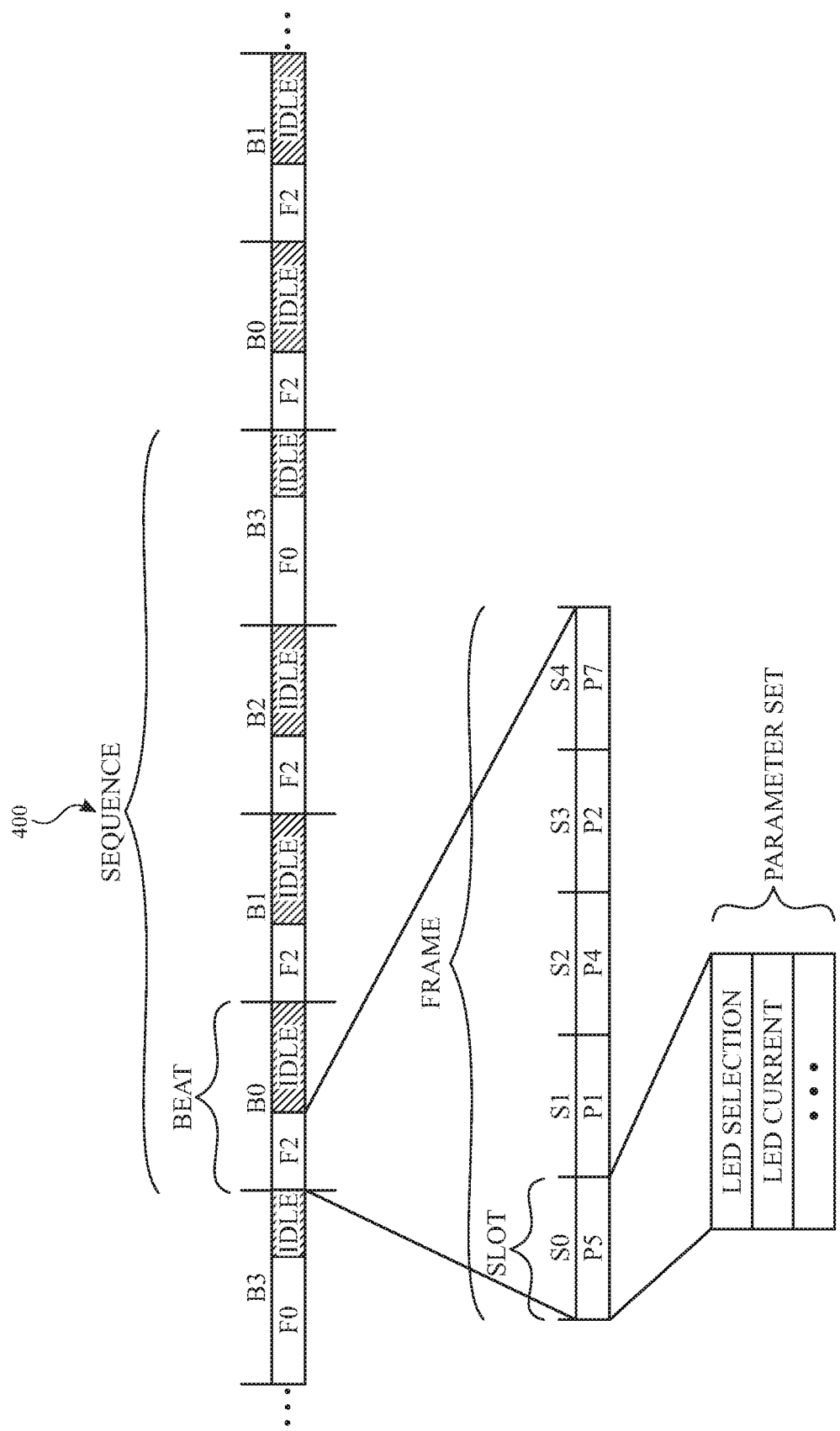
FIG. 4 illustrates a representation of a scan sequence that includes four beats according to examples of the disclosure.

As described herein, in some examples, segments/frames may be used to simplify the representation of the scan sequence. Simplifying the representation of the scan sequence can compress the number of bits and therefore registers (e.g., in register map 232) that may be required for implementing a system with multiple clients. FIG. 4 illustrates a representation of a scan sequence 400 that includes four beats according to examples of the disclosure. During each beat, one frame can be executed, optionally followed by an idle period. In FIG. 4, scan sequence 400 can include four beats labeled B0-B4 that can repeat (e.g., every four beats). Frame F2 can be executed during beats B0-B2 and frame F0 can be executed during beat B3. Each frame can include a configurable number of time slots (or slots). For example, an expansion of frame F2 is illustrated in FIG. 4 to show its five slots S0-S4. Each time slot can specify a parameter set (or multiple parameter sets if multiple LEDs and/or light paths are active or measured during the time slot). For example, frame F2 uses parameter set P5 during slot S0, parameter set P1 during slot S1, parameter set P4 during slot S2, parameter set P2 during slot S3, and parameter set P7 during slot S4. The parameter set can specify the parameters used for the measurement such as the selection of the light path (selection of an emitter and detector), emitter parameters (e.g., modulation pattern, LED current, etc.) and/or receiver parameters (e.g., receiver gain, etc.), among other possible parameters.

Representing scan sequence 400 based on its frames for each beat can be more compact than representing the scan sequence by the slots and/or parameters for each beat in the scan sequence. Additionally, the scan sequence can in some cases be further compacted by representing sequential beats configured with the same frame based on a segment specifying the frame and the number of repetitions of the frame, rather than a one-to-one correspondence of identifying a frame to perform during each beat. For example, in the scan sequence of FIG. 4, the scan can be defined using two segments by performing frame F2 three times beginning at beat B0 (a first segment) and then performing frame F0 at beat B3 (a second segment), rather than defining the scan sequence by the slots/idle periods for each of the beats in the sequence (e.g., using representations of each of the four beats configured according to a corresponding frame).

Referring back to FIG. 3A, the scan sequence of N beats can be represented by two frames. In some examples, the scan sequence can define each beat to be configured according to one of the two frames (e.g., beat 1 configured according a first frame, beat 2 configured according to the second frame, beat 3 configured according to the second frame, etc.). In some examples, the scan sequence can define the beats using two segments for the two frames; a first segment (e.g., corresponding to the first frame performed once) followed by a second segment (e.g., corresponding to the second frame performed N−1 times). In a similar manner, in FIGS. 3B-3C, the scan sequence in the first mode can be represented by one frame or one segment (which repeats each beat) and the scan sequence in the second mode can be represented by two frames (with N assignments) or two segments; a first frame (e.g., corresponding to the first segment) followed by N−1 repetitions of the second frame (e.g., corresponding to the second segment). In a similar manner, in FIG. 3D, the scan sequence can be represented by three frames (with four assignments) or four segments; a first frame F0 (e.g., corresponding to a first segment), a second frame F1 (repeating during two beats, corresponding to a second and fourth segment) and a third frame F2 (e.g., corresponding to a third segment).

FIG. 5 illustrates a representation of the scan sequence using segments according to examples of the disclosure. As shown in FIG. 5, scan sequence settings can be represented by a parameter indicative of the number of pattern segments ("FINAL_SEGMENT"), one or more parameters indicative of a frame identification ("SEG_0_FRAME," "SEG_1_FRAME," etc.), and one or more parameters indicative of frame repetitions ("SEG_0_REPS," "SEG_1_REPS," etc.). The parameters can be represented in binary format (by register bits) indexed to zero. The parameters can also include timing parameter information about the length of each beat of the scan sequence. The representation of the scan sequence can include a fixed number of register bits. The parameter indicative of the number of pattern segments can be useful to identify which of the bits in the register are applicable for the scan sequence and which of the bits are not (e.g., and can be treated as logical "don't care"). For example, the parameter "FINAL_SEGMENT" can indicate the final applicable segment (and identified frame/repetitions) and therefore the final bit registers of significance. Each pair of parameters indicative of frame identification and repetition (e.g., ("SEG_0_FRAME," "SEG 0_REPS,") can indicate the number of times to repeat the indicated frame. The pairs of parameters defining the segments can be ordered in the bit register sequence according to the sequence of the scan as shown in FIG. 5. As such, the segments can specify each beat configuration for multiple beats according to the frames without explicitly defining, in a 1:1 assignment, each beat in the scan sequence configured according to a frame).

For example, if each of these parameters were represented with three bits (for a maximum of eight pattern segments, selecting one of a maximum of eight frames, for a maximum of eight repetition per frame), the scan sequence can include up to 51 bits (3 bits for FINAL_SEGMENT and 6 bits of for the frame identifier parameter and frame repetition parameter of each of the eight possible pattern segments). Scan sequence 400 shown in FIG. 4—including three repetitions of frame F2 and then one repetition of frame F0—can then be represented by significant bits "001" (two segment patterns), "010" (identifying frame F2 as the first segment pattern), "010" (identifying two further repetitions of frame F2), "000" (identifying frame F0 as the second segment pattern), "000" (identifying no further repetitions of frame F0). The remaining 36 bits can be ignored for the scan sequence.

As another example, scan sequence 330 shown in FIG. 3D can be represented by significant bits "011" (four segment patterns), "000" (identifying frame F0 as the first segment pattern), "000" (identifying no further repetitions of frame F2), "001" (identifying frame F1 as the second segment pattern), "000" (identifying no further repetitions of frame F1), "010" (identifying frame F2 as the third segment pattern), "000" (identifying no further repetitions of frame F2), and "001" (identifying frame F1 as the fourth segment pattern), "000" (identifying no further repetitions of frame F1). The remaining 24 bits can be ignored for the scan sequence.

Referring back to FIG. 5, each of the frames identified by the scan sequence settings can be defined by frame settings. The frame settings can be represented by a parameter indicative of the number of slots in the frame ("FINAL_SLOT") and one or more parameters indicative of a parameter set identification for each respective slot ("S0_PARAMSET" for slot 0, "S1_PARAMSET" for slot 1, etc.). The parameters ("FINAL_SLOT", ("S0_PARAMSET", "S1_PARAMSET", etc.) can be represented in binary format (by register bits) indexed to zero. The representation of the frame settings can include a fixed number of register bits (determined based on the number of slots per frame and the number of bits allotted to represent the final slot and the parameter set identification for each slot). The parameter indicative of the number of slots in the frame can be useful to identify which of the bits in the register are applicable for the frame and which of the bits are not (e.g., and can be treated as logical "don't care"). For example, the parameter "FINAL_SLOT" can indicate the final applicable slot in the frame and therefore the final bit registers of significance for the frame. The slots can be ordered in the bit register sequence according to the sequence of the slots within the frame as shown in FIG. 5. Each of the slots identified by the frame settings can include a pointer to the desired parameter set setting, which can be defined by parameter set settings. The parameter set settings can be represented by a parameter indicative of the light emitter to drive ("LED ID"), and a parameter indicative of the amount of drive current ("LED_CURRENT") for the LED, among other parameters. It is understood that, in some examples, multiple LEDs may be driven with different amounts of drive current in a slot (which may be identified in one or more parameter set(s)). During operation, the scan sequence settings can indicate the applicable frame for a given beat (e.g., a pointer to the frame settings), and the driving/sensing of the optical sensor can be executed using the frame settings/parameter set settings (via pointers to the slots and/or parameter sets) corresponding to the applicable frame.

In some examples, the size of parameter set settings can be reduced by grouping some features that are common to multiple slots. For example, slot length, modulation mode, analog sensing parameters, etc., may be common to groups of LEDs, whereas LED identification and current may be more individualized. Thus, rather than larger parameter sets for each slot, smaller group parameter sets and smaller individual parameter sets can be used. In such instances, the frame can specify a group and/or individual parameter sets for each slot in the frame. In some examples, the frame can specify a parameter set and group parameters can be inferred based on the parameter set identification without requiring the frame to specify both a group parameters sets and individual parameter sets. For examples, the parameter set can be identified, and it can be inferred that parameters sets 0-3 use group 0 parameters, parameter sets 4-7 use group 1 parameters, etc.).

Referring back to FIG. 2B, it should be understood that the architecture can be implemented in various ways including hardware, firmware, software or a combination thereof. For example, scheduler 224 can be implemented in hardware as part of hardware circuitry 240 that can receive light path requirements from clients 222_1-222_N asynchronously. In some examples, the client requests themselves implemented in hardware as part of hardware circuitry 240 such that the hardware circuitry 240 receives a list of clients to activate and supplies output for each client. In some examples, sequencer 234 can be implemented as a software entity within software module 230 implemented by the processor, and the software-implemented sequencer 234 can provide the slot parameter sets to scan engine 236 prior to the execution of the next beat in the scan sequence. In some examples, sequencer 234 can be implemented in a hardware finite state machine (e.g., in a programmable logic device or field programmable gate array). In some examples, sequencer 234 can be implemented as a micro-sequencer, or CPU that can be configured to (programmed to) decode the register map and provide slot parameter sets to scan engine 236. In some examples, scan engine 236 can be implemented in a hardware finite state machine (e.g., in a programmable logic device or field programmable gate array). In some examples, scan engine 236 can be implemented as a micro-sequencer, or CPU that can be configured to (programmed to) drive and sense the optical sensor. Although shown as separate components, it should be understood that some components in the architecture of FIG. 2B can be combined. For example, sequencer 234 and scan engine 236 may be implemented in single chip that can both decode the register map and execute the driving and sensing during the various slots.

In some examples, the scanning sequence can be changed based on changing needs of clients. For example, as described above with respect to FIGS. 3B and 3C, different scan sequences can be implemented for different modes. In some examples, to reduce phase distortion in scanning, the transition between scan sequences can occur once the active scan sequence is completed (e.g., during an idle period at the end of the final beat). In some examples, the registers in the register map 232 can be written with the new scan sequence from scheduler 224 at the conclusion of the final beat in the active sequence (as indicated by sequence 234).

As discussed above, aspects in of the present technology include the gathering and use of physiological information. The technology may be implemented along with technologies that involve gathering personal data that relates to the user's health and/or uniquely identifies or can be used to contact or locate a specific person. Such personal data can include demographic data, date of birth, location-based data, telephone numbers, email addresses, home addresses, and data or records relating to a user's health or level of fitness (e.g., vital signs measurements, medication information, exercise information, etc.).

The present disclosure recognizes that a user's personal data, including physiological information, such as data generated and used by the present technology, can be used to the benefit of users. For example, a user's heart rate may allow a user to track or otherwise gain insights about their health or fitness levels.

The present disclosure contemplates that the entities responsible for the collection, analysis, disclosure, transfer, storage, or other use of such personal data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should require receipt of the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. The policies and practices may be adapted depending on the geographic region and/or the particular type and nature of personal data being collected and used.

Despite the foregoing, the present disclosure also contemplates embodiments in which users selectively block the collection of, use of, or access to, personal data, including physiological information. For example, a user may be able to disable hardware and/or software elements that collect physiological information. Further, the present disclosure contemplates that hardware and/or software elements can be provided to prevent or block access to personal data that has already been collected. Specifically, users can select to remove, disable, or restrict access to certain health-related applications collecting users' personal health or fitness data.

Therefore, according to the above, some examples of the disclosure are directed to an electronic device. The electronic device can comprise an optical sensor and processing circuitry coupled to the optical sensor. The optical sensor can comprise: a plurality of light emitters configured to illuminate at one or more wavelengths; and a plurality of light detectors configured to detect the return of the light (e.g., reflections and/or scattering) from the one or more emitters. The processing circuitry can be configured to receive a first request to perform a first plurality of optical measurements using the optical sensor, the first plurality of optical measurements including one or more first optical measurements corresponding to a first sensing client at a first scan rate and one or more second optical measurements corresponding to a second sensing client at a second scan rate different from the first scan rate. In response to the first request to perform the first plurality of optical measurements, the processing circuitry can generate a scan sequence configured to multiplex the optical sensor for the first plurality of optical measurements; and perform the first plurality of optical measurements according to the scan sequence. Additionally or alternatively to one or more of the examples disclosed above, in some examples, the first sensing client can be a physiological signal client that estimates a characteristic of a user's physiological signal and the second sensing client can be a non-physiological signal client. Additionally or alternatively to one or more of the examples disclosed above, in some examples, the first sensing client can be a first physiological signal client that estimates a first characteristic of a first physiological signal of a user and the second sensing client can be a second physiological signal client that estimates a second characteristic of a second physiological signal of the user. Additionally or alternatively to one or more of the examples disclosed above, in some examples, the first plurality of optical measurements can further include one or more third optical measurements corresponding to a third sensing client at a third scan rate different from the first scan rate and the second scan rate. Additionally or alternatively to one or more of the examples disclosed above, in some examples, the scan sequence can define a plurality of beats and can identify a frame to perform during each of the plurality of beats. Additionally or alternatively to one or more of the examples disclosed above, in some examples, the one or more first optical measurements can be performed during a first beat in the scan sequence and the one or more second optical measurements can be divided between two beats. Additionally or alternatively to one or more of the examples disclosed above, in some examples, the one or more first optical measurements can be completed during each beat in the scan sequence and the one or more second optical measurements can be completed for alternating beats in the scan sequence. Additionally or alternatively to one or more of the examples disclosed above, in some examples, the processing circuitry can be further configured to: receive a second request to perform a second plurality of optical measurements using the optical sensor, the second plurality of optical measurements different from the first plurality of optical measurements; and in response to the second request to perform the second plurality of optical measurements: generate a second scan sequence configured to multiplex the optical sensor for the second plurality of optical measurements; and perform the second plurality of optical measurements according to the scan sequence. Additionally or alternatively to one or more of the examples disclosed above, in some examples, the second request can correspond to an asynchronous request from one or more clients, and the second scan sequence generated in response to the second request can be performed beginning at the conclusion of the performance of the first plurality of optical measurements. Additionally or alternatively to one or more of the examples disclosed above, in some examples, the processing circuitry can comprise a scheduler configured to generate the scan sequence. Additionally or alternatively to one or more of the examples disclosed above, in some examples, the processing circuitry can comprise a plurality of registers configured to store the scan sequence. Additionally or alternatively to one or more of the examples disclosed above, in some examples, the processing circuitry can comprises: a scan engine configured to perform the first plurality of optical measurements according to the scan sequence; and a sequencer configured to track the scan sequence, decode the plurality of registers, and provide slot and parameter set information to the scan engine. Additionally or alternatively to one or more of the examples disclosed above, in some examples, the scan sequence stored in the plurality of registers can be represented as a plurality of bits representing one or more frame identity parameters and one or more corresponding frame repetition parameters. Additionally or alternatively to one or more of the examples disclosed above, in some examples, a slot sequence stored in the plurality of registers corresponding to a respective frame can be represented as a plurality of bits representing one or more parameter set parameters. Additionally or alternatively to one or more of the examples disclosed above, in some examples, the slot sequence stored in the plurality of registers corresponding to the respective frame can be further represented as one or more additional bits representing one or more group parameter set parameters or the one or more group parameter set parameters can be inferred from the plurality of bits representing the one or more parameter set parameters.

Some examples of the disclosure are directed to a method. The method can comprise: receiving a first request to perform a first plurality of optical measurements using an optical sensor, the first plurality of optical measurements including one or more first optical measurements corresponding to a first sensing client at a first scan rate and one or more second optical measurements corresponding to a second sensing client at a second scan rate different from the first scan rate. The method can further comprise: in response to the first request to perform the first plurality of optical measurements: generating a scan sequence configured to multiplex the optical sensor for the first plurality of optical measurements; and performing the first plurality of optical measurements according to the scan sequence. Additionally or alternatively to one or more of the examples disclosed above, in some examples, the first sensing client can be a physiological signal client that estimates a characteristic of a user's physiological signal and the second sensing client can be a non-physiological signal client. Additionally or alternatively to one or more of the examples disclosed above, in some examples, the first sensing client can be a first physiological signal client that estimates a first characteristic of a first physiological signal of a user and the second sensing client can be a second physiological signal client that estimates a second characteristic of a second physiological signal of the user. Additionally or alternatively to one or more of the examples disclosed above, in some examples, the first plurality of optical measurements can further include one or more third optical measurements corresponding to a third sensing client at a third scan rate different from the first scan rate and the second scan rate. Additionally or alternatively to one or more of the examples disclosed above, in some examples, the scan sequence can define a plurality of beats and can identify a frame to perform during each of the plurality of beats. Additionally or alternatively to one or more of the examples disclosed above, in some examples, the one or more first optical measurements can be performed during a first beat in the scan sequence and the one or more second optical measurements can be divided between two beats. Additionally or alternatively to one or more of the examples disclosed above, in some examples, the one or more first optical measurements can be completed during each beat in the scan sequence and the one or more second optical measurements can be completed for alternating beats in the scan sequence. Additionally or alternatively to one or more of the examples disclosed above, in some examples, the method can further comprise: receiving a second request to perform a second plurality of optical measurements using the optical sensor, the second plurality of optical measurements different from the first plurality of optical measurements; and in response to the second request to perform the second plurality of optical measurements: generating a second scan sequence configured to multiplex the optical sensor for the second plurality of optical measurements; and performing the second plurality of optical measurements according to the scan sequence. Additionally or alternatively to one or more of the examples disclosed above, in some examples, the second request can corresponds to an asynchronous request from one or more clients, and the second scan sequence generated in response to the second request can be performed beginning at the conclusion of the performance of the first plurality of optical measurements. Additionally or alternatively to one or more of the examples disclosed above, in some examples, the method can further comprise storing the scan sequence in a plurality of registers. Additionally or alternatively to one or more of the examples disclosed above, in some examples, the method can further comprise decoding the plurality of registers to provide slot and parameter set information for performing the first plurality of optical measurements. Additionally or alternatively to one or more of the examples disclosed above, in some examples, the scan sequence stored in the plurality of registers can be represented as a plurality of bits representing one or more frame identity parameters and one or more corresponding frame repetition parameters. Additionally or alternatively to one or more of the examples disclosed above, in some examples, a slot sequence stored in the plurality of registers corresponding to a respective frame can be represented as a plurality of bits representing one or more parameter set parameters. Additionally or alternatively to one or more of the examples disclosed above, in some examples, the slot sequence stored in the plurality of registers corresponding to the respective frame can be further represented as one or more additional bits representing one or more group parameter set parameters or the one or more group parameter set parameters can be inferred from the plurality of bits representing the one or more parameter set parameters.

Some examples of the disclosure are directed to a non-transitory computer readable storage medium. The non-transitory computer readable storage medium can store instructions, which when executed by a device comprising an optical sensor and one or more processing circuits, can cause the one or more processing circuits to perform any of the above methods.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

What is claimed is:

1. An electronic device comprising:
an optical sensor comprising:
  a plurality of light emitters configured to illuminate at one or more wavelengths; and
  a plurality of light detectors configured to detect returning light; and
processing circuitry coupled to the optical sensor and configured to:
  receive a first request to perform a first plurality of optical measurements using the optical sensor, the first plurality of optical measurements including one or more first optical measurements corresponding to a first sensing client at a first scan rate and one or more second optical measurements corresponding to a second sensing client at a second scan rate different from the first scan rate; and
  in response to the first request to perform the first plurality of optical measurements:
    generate a scan sequence configured to multiplex the optical sensor for the first plurality of optical measurements; and
    perform the first plurality of optical measurements according to the scan sequence.

2. The electronic device of claim 1, wherein the first sensing client is a physiological signal client that estimates a characteristic of a user's physiological signal and the second sensing client is a non-physiological signal client.

3. The electronic device of claim 1, wherein the first sensing client is a first physiological signal client that estimates a first characteristic of a first physiological signal of a user and the second sensing client is a second physiological signal client that estimates a second characteristic of a second physiological signal of the user.

4. The electronic device of claim 1, the first plurality of optical measurements further including one or more third optical measurements corresponding to a third sensing client at a third scan rate different from the first scan rate and the second scan rate.

5. The electronic device of claim 1, wherein the scan sequence defines a plurality of beats and identifies a frame to perform during each of the plurality of beats.

6. The electronic device of claim 5, wherein the one or more first optical measurements are performed during a first beat in the scan sequence and the one or more second optical measurements are divided between two beats.

7. The electronic device of claim 5, wherein the one or more first optical measurements are completed during each beat in the scan sequence and the one or more second optical measurements are completed for alternating beats in the scan sequence.

8. The electronic device of claim 1, the processing circuitry further configured to:
  receive a second request to perform a second plurality of optical measurements using the optical sensor, the second plurality of optical measurements different from the first plurality of optical measurements; and
  in response to the second request to perform the second plurality of optical measurements:
    generate a second scan sequence configured to multiplex the optical sensor for the second plurality of optical measurements; and
    perform the second plurality of optical measurements according to the scan sequence.

9. The electronic device of claim 8, wherein the second request corresponds to an asynchronous request from one or more clients, and wherein the second scan sequence generated in response to the second request is performed beginning at the conclusion of the performance of the first plurality of optical measurements.

10. The electronic device of claim 1, wherein the processing circuitry comprises a scheduler configured to generate the scan sequence.

11. The electronic device of claim 1, wherein the processing circuitry comprises a plurality of registers configured to store the scan sequence.

12. The electronic device of claim 11, wherein the processing circuitry comprises:
  a scan engine configured to perform the first plurality of optical measurements according to the scan sequence; and
  a sequencer configured to track the scan sequence, decode the plurality of registers, and provide slot and parameter set information to the scan engine.

13. The electronic device of claim 11, wherein the scan sequence stored in the plurality of registers is represented as a plurality of bits representing one or more frame identity parameters and one or more corresponding frame repetition parameters.

14. The electronic device of claim 13, wherein a slot sequence stored in the plurality of registers corresponding to a respective frame is represented as a plurality of bits representing one or more parameter set parameters.

15. The electronic device of claim 14, wherein the slot sequence stored in the plurality of registers corresponding to the respective frame is further represented as one or more additional bits representing one or more group parameter set parameters or wherein the one or more group parameter set parameters are inferred from the plurality of bits representing the one or more parameter set parameters.

16. A method comprising:
receiving a first request to perform a first plurality of optical measurements using an optical sensor, the first plurality of optical measurements including one or more first optical measurements corresponding to a first sensing client at a first scan rate and one or more second optical measurements corresponding to a second sensing client at a second scan rate different from the first scan rate; and
in response to the first request to perform the first plurality of optical measurements:
generating a scan sequence configured to multiplex the optical sensor for the first plurality of optical measurements; and
performing the first plurality of optical measurements according to the scan sequence.

17. The method of claim 16, wherein the first sensing client is a physiological signal client that estimates a characteristic of a user's physiological signal and the second sensing client is a non-physiological signal client.

18. The method of claim 16, wherein the first sensing client is a first physiological signal client that estimates a first characteristic of a first physiological signal of a user and the second sensing client is a second physiological signal client that estimates a second characteristic of a second physiological signal of the user.

19. The method of claim 16, the first plurality of optical measurements further including one or more third optical measurements corresponding to a third sensing client at a third scan rate different from the first scan rate and the second scan rate.

20. The method of claim 16, wherein the scan sequence defines a plurality of beats and identifies a frame to perform during each of the plurality of beats.

21. The method of claim 20, wherein the one or more first optical measurements are performed during a first beat in the scan sequence and the one or more second optical measurements are divided between two beats.

22. The method of claim 20, wherein the one or more first optical measurements are completed during each beat in the scan sequence and the one or more second optical measurements are completed for alternating beats in the scan sequence.

23. The method of claim 16, further comprising:
receiving a second request to perform a second plurality of optical measurements using the optical sensor, the second plurality of optical measurements different from the first plurality of optical measurements; and
in response to the second request to perform the second plurality of optical measurements:
generating a second scan sequence configured to multiplex the optical sensor for the second plurality of optical measurements; and
performing the second plurality of optical measurements according to the scan sequence.

24. The method of claim 23, wherein the second request corresponds to an asynchronous request from one or more clients, and wherein the second scan sequence generated in response to the second request is performed beginning at the conclusion of the performance of the first plurality of optical measurements.

25. A non-transitory computer readable storage medium storing instructions, which when executed by a device comprising an optical sensor and one or more processing circuits, cause the one or more processing circuits to:
receive a first request to perform a first plurality of optical measurements using an optical sensor, the first plurality of optical measurements including one or more first optical measurements corresponding to a first sensing client at a first scan rate and one or more second optical measurements corresponding to a second sensing client at a second scan rate different from the first scan rate; and
in response to the first request to perform the first plurality of optical measurements:
generate a scan sequence configured to multiplex the optical sensor for the first plurality of optical measurements; and
perform the first plurality of optical measurements according to the scan sequence.

26. The non-transitory computer readable storage medium of claim 25, wherein the first sensing client is a physiological signal client that estimates a characteristic of a user's physiological signal and the second sensing client is a non-physiological signal client.

27. The non-transitory computer readable storage medium of claim 25, wherein the first sensing client is a first physiological signal client that estimates a first characteristic of a first physiological signal of a user and the second sensing client is a second physiological signal client that estimates a second characteristic of a second physiological signal of the user.

28. The non-transitory computer readable storage medium of claim 25, the first plurality of optical measurements further including one or more third optical measurements corresponding to a third sensing client at a third scan rate different from the first scan rate and the second scan rate.

29. The non-transitory computer readable storage medium of claim 25, wherein the scan sequence defines a plurality of beats and identifies a frame to perform during each of the plurality of beats.

30. The non-transitory computer readable storage medium of claim 29, wherein the one or more first optical measurements are performed during a first beat in the scan sequence and the one or more second optical measurements are divided between two beats.

31. The non-transitory computer readable storage medium of claim 29, wherein the one or more first optical measurements are completed during each beat in the scan sequence and the one or more second optical measurements are completed for alternating beats in the scan sequence.

32. The non-transitory computer readable storage medium of claim 25, wherein the instructions, when executed by the device, cause the one or more processing circuits to:
receive a second request to perform a second plurality of optical measurements using the optical sensor, the second plurality of optical measurements different from the first plurality of optical measurements; and in response to the second request to perform the second plurality of optical measurements:

generate a second scan sequence configured to multiplex the optical sensor for the second plurality of optical measurements; and perform the second plurality of optical measurements according to the scan sequence.

33. The non-transitory computer readable storage medium of claim 32, wherein the second request corresponds to an asynchronous request from one or more clients, and wherein the second scan sequence generated in response to the second request is performed beginning at the conclusion of the performance of the first plurality of optical measurements.

* * * * *